(12) United States Patent
Sugahara

(10) Patent No.: US 12,133,753 B2
(45) Date of Patent: Nov. 5, 2024

(54) IMAGING SUPPORT DEVICE, OPERATION METHOD FOR THE SAME AND OPERATION PROGRAM

(71) Applicant: FUJIFILM CORPORATION, Tokyo (JP)

(72) Inventor: Masataka Sugahara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 251 days.

(21) Appl. No.: 17/950,110

(22) Filed: Sep. 22, 2022

(65) Prior Publication Data

US 2023/0016072 A1  Jan. 19, 2023

Related U.S. Application Data

(63) Continuation of application No. PCT/JP2021/009669, filed on Mar. 10, 2021.

(30) Foreign Application Priority Data

Mar. 30, 2020  (JP) .................................. 2020-061593

(51) Int. Cl.
*A61B 6/00* (2024.01)
*A61B 6/04* (2006.01)
*A61B 6/46* (2024.01)

(52) U.S. Cl.
CPC ................ *A61B 6/488* (2013.01); *A61B 6/04* (2013.01); *A61B 6/461* (2013.01); *A61B 6/5211* (2013.01); *A61B 6/54* (2013.01)

(58) Field of Classification Search
None
See application file for complete search history.

(56) References Cited

U.S. PATENT DOCUMENTS 11,475,991 B2 * 10/2022 Laaksonen ............. G16H 20/40
2017/0337682 A1 * 11/2017 Liao ...................... A61B 5/7267
(Continued)

FOREIGN PATENT DOCUMENTS

| CN | 109730704 A | 5/2019 |
| JP | 2019-033830 A | 3/2019 |

(Continued)

OTHER PUBLICATIONS

English language translation of the following: Office action dated Jul. 4, 2023 from the JPO in a Japanese patent application No. 2022-511748 corresponding to the instant patent application.
(Continued)

*Primary Examiner* — Marcus H Taningco
(74) *Attorney, Agent, or Firm* — SOLARIS Intellectual Property Group, PLLC

(57) ABSTRACT

An imaging support device used in a radiography apparatus including a radiation source and a radiation image detector that detects a radiation image of a subject on the basis of radiation emitted from the radiation source and transmitted through the subject, and includes an optical camera that outputs an optical image by optically imaging a region including an irradiation field of the radiation applied to the subject from the radiation source, and at least one processor, in which the processor executes a determination process of determining a possibility of reimaging in a case where radiography is performed on the basis of the optical image acquired by the optical camera before start of the radiography by using a trained model that has learned a relationship between the optical image captured during the radiography and a necessity of recapturing the radiation image that is captured during the radiography.

9 Claims, 11 Drawing Sheets

(56) References Cited

U.S. PATENT DOCUMENTS

| | | | |
|---|---|---|---|
| 2019/0046130 A1 | 2/2019 | Imamura et al. | |
| 2019/0183439 A1 | 6/2019 | Joerger et al. | |
| 2019/0209106 A1 | 7/2019 | Bechtold et al. | |
| 2020/0187876 A1 | 6/2020 | Imamura et al. | |
| 2020/0205766 A1 | 7/2020 | Wu et al. | |
| 2021/0161501 A1 | 6/2021 | Sendai | |
| 2021/0369229 A1 | 12/2021 | Okumura | |
| 2022/0160322 A1* | 5/2022 | Homan | A61B 6/487 |

FOREIGN PATENT DOCUMENTS

| | | | |
|---|---|---|---|
| JP | 2020-199163 A | 12/2020 | |
| KR | 10-2020-0023968 A | 3/2020 | |
| WO | 2019/208006 A1 | 10/2019 | |
| WO | 2020036225 A1 | 2/2020 | |

OTHER PUBLICATIONS

Extended European Search Report dated Aug. 25, 2023, issued in corresponding EP Patent Application No. 21782317.8.
International Search Report issued in International Application No. PCT/JP2021/009669 on May 18, 2021.
Written Opinion of the ISA issued in International Application No. PCT/JP2021/009669 on May 18, 2021.

* cited by examiner

IMAGING SUPPORT DEVICE, OPERATION METHOD FOR THE SAME AND OPERATION PROGRAM

CROSS-REFERENCE TO RELATED APPLICATIONS

This application is a continuation application of International Application No. PCT/JP2021/009669, filed on Mar. 10, 2021, the disclosure of which is incorporated herein by reference in its entirety. Further, this application claims priority from Japanese Patent Application No. 2020-061593, filed on Mar. 30, 2020, the disclosure of which is incorporated herein by reference in its entirety.

BACKGROUND

1. Technical Field

The technique of the present disclosure relates to an imaging support device, an operation method for the same, and an operation program.

2. Description of the Related Art

In a radiography system used in the medical field, a radiologist or a doctor (hereinafter referred to as a technician or the like) positions an imaging site of a subject in preparation for imaging, and then radiography is performed on the basis of instructions from the technician or the like. However, after positioning an imaging site with respect to an irradiation field of radiation and before radiography is performed, the subject may move to cause a misregistration of an imaging site, and an image of a desired imaging site may not be obtained. For a site where positioning is difficult, such as a side of a joint, even though a technician or the like thinks that positioning has been performed accurately, actually, a slight misregistration may occur.

As described above, in a case where a misregistration of an imaging site occurs, a desired radiation image may not be obtained. A failure to obtain a desired radiation image through radiography, that is, a failure in radiography is referred to as an "imaging failure". In a case where there is imaging failure, reimaging will be performed. The reimaging preferably takes less time and effort.

In order to reduce the number of times of reimaging of a subject due to such radiation, there is a technique in which an optical camera that captures an optical image of a subject is provided and an amount of misregistration of the subject is detected on the basis of the optical image of the subject in an imaging preparation stage (refer to JP2019-033830A). In a radiography system disclosed in JP2019-033830A, a positioning index image indicating a set position which is an ideal position of a subject with respect to a radiation detector is registered in advance, and an amount of misregistration of the subject is detected on the basis of the positioning index image and the optical image. In the radiography system disclosed in JP2019-033830A, in a case where the amount of misregistration is more than a threshold value, and radiography is performed without any adjustment, there is concern that an imaging failure will occur and reimaging will be required. Therefore, a warning prompting a user to reposition the subject is reported.

SUMMARY

According to the technique disclosed in JP2019-033830A, it is possible to ascertain a possibility of reimaging at the time of preparation for imaging before radiography. However, in the technique disclosed in JP2019-033830A, in order to deal with various subjects, it is necessary to register various positioning index images according to characteristics of subjects. For example, in a case where an imaging site is the knee, a width of the knee or the like differs depending on the physique of a patient as a subject, and thus it is necessary to register various positioning index images according to various physiques.

Therefore, in the technique described in JP2019-033830A, in addition to the need to register various positioning index images in advance, it is necessary to select a positioning index image suitable for a subject, which is troublesome. As described above, the technique disclosed in JP2019-033830A cannot easily ascertain a possibility of reimaging at the time of preparation for imaging.

An object of the technique of the present disclosure is to provide an imaging support device, an operation method for the same, and an operation program that make it possible to easily ascertain a possibility of reimaging at the time of preparing for imaging before radiography.

In order to achieve the above object, according to the present disclosure, there is provided an imaging support device used in a radiography apparatus including a radiation source and a radiation image detector that detects a radiation image of a subject on the basis of radiation emitted from the radiation source and transmitted through the subject, the imaging support device including an optical camera that outputs an optical image by optically imaging a region including an irradiation field of the radiation applied to the subject from the radiation source; and at least one processor, in which the processor executes a determination process of determining a possibility of reimaging in a case where radiography is performed on the basis of the optical image acquired by the optical camera before start of the radiography by using a trained model that has learned a relationship between the optical image captured during the radiography and a necessity of recapturing the radiation image that is captured during the radiography.

It is preferable that the processor executes a warning notification process of providing a notification of a warning in a case where it is determined in the determination process that there is a possibility of reimaging.

It is preferable that the processor executes a prohibition process of prohibiting irradiation from the radiation source in a case where it is determined in the determination process that there is a possibility of reimaging.

It is preferable that the processor executes a presentation process of presenting a corrective measure for correcting a position or an orientation of the subject.

It is preferable that, in the presentation process, the processor presents a reason for determining that there is a possibility of reimaging in addition to the corrective measure.

It is preferable that, in the presentation process, the processor displays at least one of the corrective measure or the reason on a display.

It is preferable that the processor executes an association process of associating the optical image captured during the radiography with result information indicating whether or not the radiation image captured during the radiography has been recaptured.

According to the present disclosure, there is provided an operation method for an imaging support device used in a radiography apparatus including a radiation source and a radiation image detector that detects a radiation image of a subject on the basis of radiation emitted from the radiation source and transmitted through the subject, the imaging support device including an optical camera that optically images a region including an irradiation field of the radiation applied to the subject from the radiation source, the operation method including determining a possibility of reimaging in a case where radiography is performed on the basis of the optical image acquired by the optical camera before start of the radiography by using a trained model that has learned a relationship between the optical image captured during the radiography and a necessity of recapturing the radiation image that is captured during the radiography.

According to the present disclosure, there is provided an operation program for operating an imaging support device used in a radiography apparatus including a radiation source and a radiation image detector that detects a radiation image of a subject on the basis of radiation emitted from the radiation source and transmitted through the subject, the imaging support device including an optical camera that optically images a region including an irradiation field of the radiation applied to the subject from the radiation source and at least one processor, the operation program causing the processor to execute a determination process of determining a possibility of reimaging in a case where radiography is performed on the basis of the optical image acquired by the optical camera before start of the radiography by using a trained model that has learned a relationship between the optical image captured during the radiography and a necessity of recapturing the radiation image that is captured during the radiography.

According to the technique of the present disclosure, it is possible to provide an imaging support device, an operation method for the same, and an operation program that make it possible to easily ascertain a possibility of reimaging at the time of preparation for imaging before radiography.

BRIEF DESCRIPTION OF THE DRAWINGS

Exemplary embodiments according to the technique of the present disclosure will be described in detail based on the following figures, wherein.

DETAILED DESCRIPTION

Figure 1:
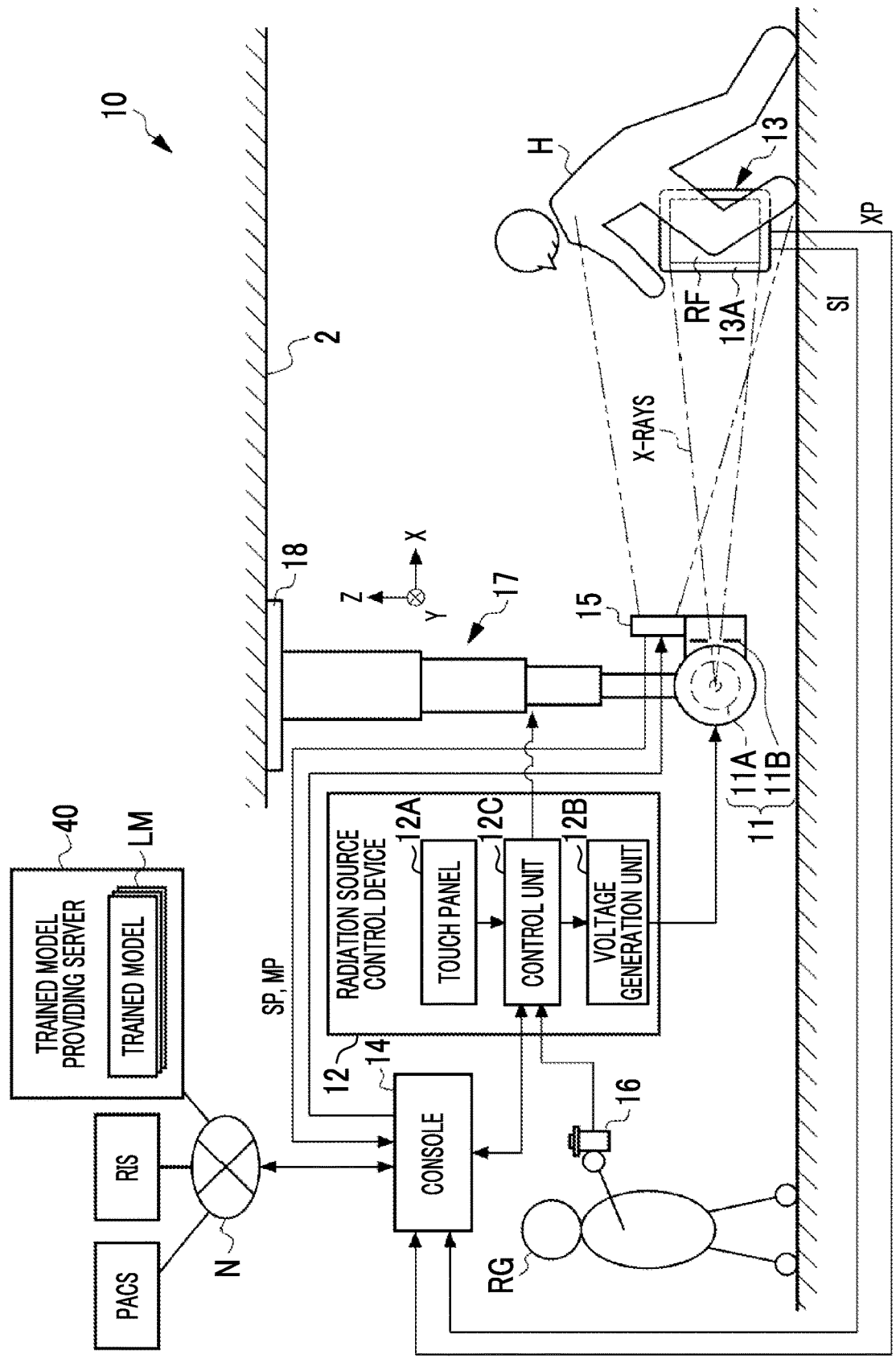
FIG. 1 is a diagram showing a configuration of an X-ray imaging system.

FIG. 1 shows a configuration of an X-ray imaging system 10 that uses X-rays as radiation. In FIG. 1, an X-ray imaging system 10 using X-rays as radiation includes an X-ray source 11, a radiation source control device 12, an electronic cassette 13, a console 14, and an optical camera 15. In the present embodiment, an imaging support device is configured by the console 14 and the optical camera 15. The X-ray source 11 is an example of a radiation source. The electronic cassette 13 is an example of a radiation image detector.

In the X-ray imaging system 10, the electronic cassette 13 is disposed at a position facing the X-ray source 11. By disposing a subject H between the X-ray source 11 and the electronic cassette 13, it is possible to capture an X-ray image of an imaging site (knee in FIG. 1) of the subject H. The X-ray source 11 and the electronic cassette 13 configure an X-ray imaging apparatus. This X-ray imaging apparatus is an example of a radiography apparatus according to the technique of the present disclosure.

The electronic cassette 13 may be arranged on a standing position imaging table or a lying position imaging table. In the present embodiment, it is assumed that a radiologist (hereinafter, simply referred to as a technician) RG positions the subject H, and then the technician RG performs an X-ray imaging operation.

The X-ray source 11 includes an X-ray tube 11A that generates X-rays and an irradiation field limiter 11B that limits an irradiation field RF that is a region irradiated with X-rays. The X-ray source 11 may include an irradiation field display light source (not shown) that emits irradiation field display light indicating the irradiation field RF on an X-ray incident surface 13A of the electronic cassette 13.

The X-ray tube 11A has a filament that emits thermions and a target that collides with the thermions emitted from the filament and emits X-rays. In the irradiation field limiter 11B, for example, by disposing four lead plates that shield X-rays on respective quadrangular sides, a quadrangular irradiation opening for transmitting X-rays is formed at the center. In this case, the irradiation field limiter 11B changes a size of the irradiation opening by moving positions of the lead plates, and sets the irradiation field RF.

The radiation source control device 12 has a touch panel 12A, a voltage generation unit 12B, and a control unit 12C. The touch panel 12A is operated by the technician RG in a case where X-rays irradiation conditions and a size of the irradiation opening of the irradiation field limiter 11B are set. The X-ray irradiation conditions include a tube voltage and a tube current applied to the X-ray source 11, and the X-ray irradiation time.

The voltage generation unit 12B generates a tube voltage applied to the X-ray tube 11A. By controlling an operation of the voltage generation unit 12B, the control unit 12C sets the tube voltage, the tube current, and the X-ray irradiation time to values set by using the touch panel 12A. The control unit 12C has a timer that starts clocking in a case where X-rays are generated from the X-ray tube 11A. The control unit 12C stops the operation of the X-ray tube 11A, for example, when the time measured by the timer reaches the irradiation time defined in the irradiation conditions. The control unit 12C operates the irradiation field limiter 11B, and sets the size of the irradiation opening to a size set by using the touch panel 12A.

An irradiation switch 16 is connected to the control unit 12C via a cable or the like. The irradiation switch 16 is operated by the technician RG in a case where irradiation of X-rays is started. In a case where the irradiation switch 16 is operated, the radiation source control device 12 generates X-rays in the X-ray tube 11A. Consequently, X-rays are applied toward the irradiation field RF.

The electronic cassette 13 detects an X-ray image XP on the basis of X-rays emitted from the X-ray source 11 and transmitted through the imaging site of the subject H. The electronic cassette 13 has a wireless communication unit and a battery, and performs an operation wirelessly. The electronic cassette 13 wirelessly transmits the detected X-ray image XP to the console 14. The X-ray image XP is an example of a radiation image.

The X-ray source 11 is suspended vertically downward from a ceiling 2 of an imaging room. The X-ray source 11 is held by a suspension holding mechanism 17. The suspension holding mechanism 17 is attached to the ceiling 2 via a horizontal movement mechanism 18. The suspension holding mechanism 17 holds the X-ray source 11 in a vertical direction (±Z direction) to be able to be moved up and down. The horizontal movement mechanism 18 movably holds the suspension holding mechanism 17 in an X-ray irradiation axis direction (±X direction) and a direction (±Y direction) orthogonal to the X-ray irradiation axis direction of the X-ray source 11.

A motor (not shown) is provided in each of the suspension holding mechanism 17 and the horizontal movement mechanism 18, and it is possible to move the X-ray source 11 manually or electrically in each direction. Operations of the suspension holding mechanism 17 and the horizontal movement mechanism 18 are controlled by the control unit 12C. Whether to move the X-ray source 11 manually or electrically may be selected by using the touch panel 12A. By moving the X-ray source 11, a position of the irradiation field RF can be adjusted.

The optical camera 15 is an optical digital camera configured to include a complementary metal oxide semiconductor (CMOS) type image sensor or a charge coupled device (CCD) type image sensor, and performing imaging on the basis of visible light as an example. The optical camera 15 enables still image capturing and motion picture capturing. The optical camera 15 is an example of a motion picture capturing device according to the technique of the present disclosure.

An optical axis of the optical camera 15 is parallel to the irradiation axis of X-rays passing through the center of the irradiation field RF. The optical camera 15 generates an optical image by optically imaging a region including the irradiation field RF. The optical image is an image indicating the imaging site of the subject H located in the irradiation field RF. The optical image is, for example, a color still image or motion picture.

The optical camera 15 is attached to an outer peripheral portion of the X-ray source 11. The optical camera 15 does not have to be attached to the outer peripheral portion of the X-ray source 11, or may be built in the X-ray source 11. In the optical camera 15, an objective lens and an imaging element may be configured separately. In this case, the objective lens may be disposed on the outer peripheral portion of the X-ray source 11 and the imaging element may be built in a portion other than the X-ray source 11 (for example, an arm supporting the X-ray source 11).

The optical camera 15 is connected to the console 14 by wire or wirelessly. The console 14 functions as an imaging control device to control an imaging operation of the optical camera 15. The console 14 causes the optical camera 15 to capture a still image in conjunction with X-ray imaging, and also to capture a motion picture during an imaging preparation period before the start of the X-ray imaging. For example, the console 14 is installed in an operation room adjacent to the imaging room in which the X-ray source 11 is installed.

The console 14 transmits a still image capturing command signal to the optical camera 15 in a case where the irradiation switch 16 is operated. The optical camera 15 captures a still image of a region including the irradiation field RF in response to the still image capturing command signal input from the console 14. An optical image (hereinafter, referred to as a still image SP) obtained through this still image capturing is transmitted to the console 14.

The console 14 transmits a motion picture capturing start signal to the optical camera 15 in a case where an operation of starting imaging preparation is performed by the technician RG. The optical camera 15 starts to capture a motion picture of a region including the irradiation field RF in response to the motion picture capturing start signal input from the console 14. An optical image (hereinafter, referred to as a motion picture MP) obtained through this motion picture capturing is transmitted to the console 14 as a so-called live view image in real time at the time of motion picture capturing.

The console 14 is connected to a radiology information system (RIS) and a picture archiving and communication system (PACS) provided in the X-ray imaging system 10 via the network N. The console 14 may be connected to an imaging failure management system via the network N. The imaging failure management system collects the X-ray image XP labeled as imaging failure and analyzes an imaging failure ratio, a cause of the imaging failure, and the like.

The console 14 has a function of performing X-ray imaging by an operation of the technician RG on the basis of an imaging order, various types of information, and the like acquired from the RIS. The console 14 has a function of outputting the X-ray image XP received from the electronic cassette 13 to the PACS after the X-ray imaging. The console 14 outputs the motion picture MP acquired at the same time as the X-ray image XP at the time of X-ray imaging in association with the X-ray image XP.

For example, the console 14 is installed in an operation room adjacent to the imaging room in which the X-ray source 11 is installed. The X-ray image XP received by the console 14 from the electronic cassette 13 is displayed on the display 30 (refer to FIG. 3) provided on the console 14. The technician RG can determine whether or not the X-ray image XP is an image suitable for diagnosis on the basis of the X-ray image XP displayed on the display 30.

The console 14 is connected to a trained model providing server 40 via the network N. The trained model providing server 40 stores the trained model LM that has learned a relationship between the still image SP captured at the time of X-ray imaging and the necessity of reimaging the X-ray image XP captured at the time of X-ray imaging. In a case where the console 14 uses the trained model LM provided by the trained model providing server 40 to determine whether or not there is a possibility that reimaging is necessary on the basis of each frame obtained at the time of motion picture capturing in a case where X-ray imaging is performed in a state of the subject H represented by each frame. That is, every time one frame is acquired at the time of motion picture capturing during the imaging preparation period before the start of X-ray imaging, in a case where the X-ray imaging is performed at the time of acquiring the frame, the console 14 determines whether or not there is a possibility that reimaging is necessary.

A plurality of learned trained models LM are stored in the trained model providing server 40. For example, each of the plurality of trained models LM is associated with an imaging technique. The imaging technique is information regarding an imaging site of the subject H and a posture and an orientation of the imaging site. For example, the trained model LM is a model generated by performing machine learning by using the still image SP stored in the PACS and stored in association with the X-ray image XP captured according to the same imaging technique. Machine learning for generating the trained model LM is performed, for example, on the trained model providing server 40.

Figure 2:
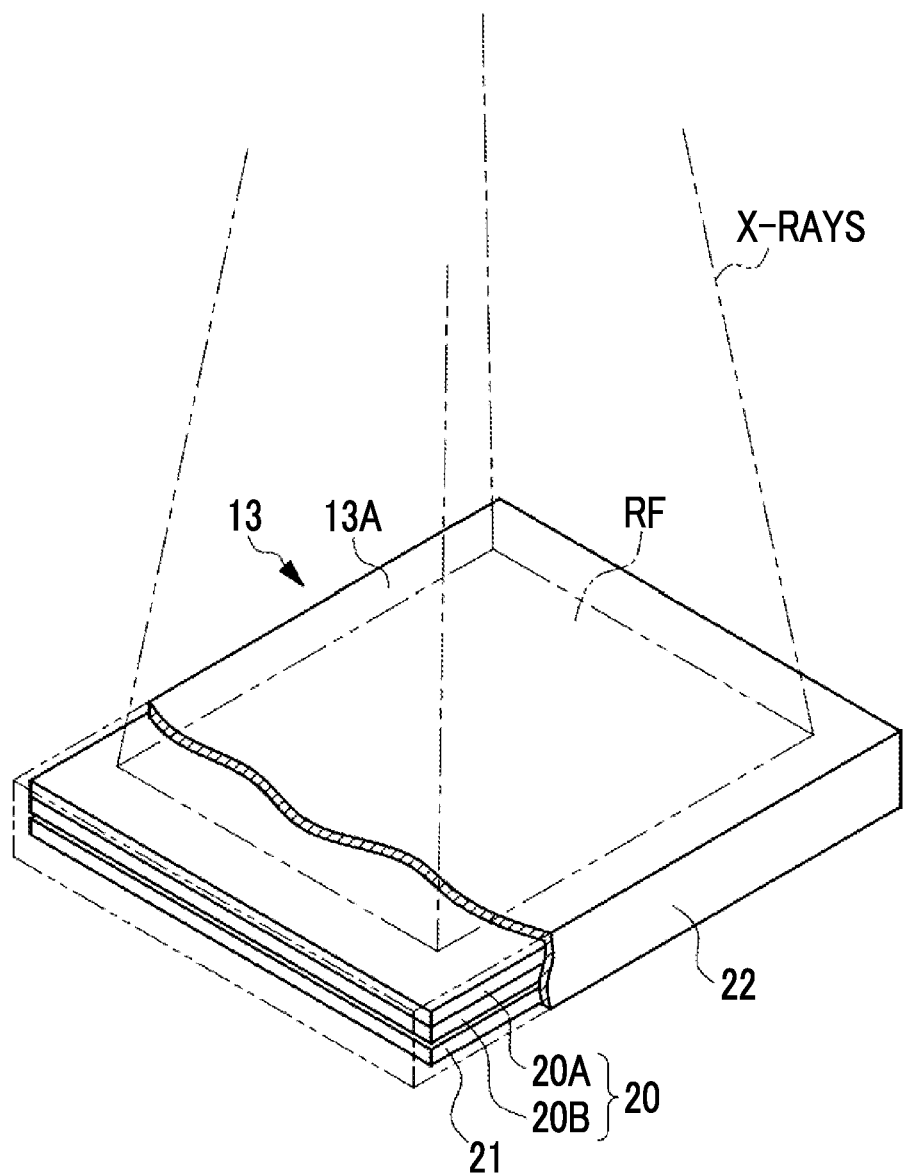
FIG. 2 is an external perspective view of an electronic cassette.

In FIG. 2, the electronic cassette 13 includes a sensor panel 20, a circuit unit 21, and a rectangular parallelepiped-shaped portable casing 22 that accommodates the sensor panel 20 and the circuit unit 21. The casing 22 has a size conforming to the international standard International Organization for Standardization (ISO) 4090:2001, which is substantially the same as that of, for example, a film cassette, an imaging plate (IP) cassette, or a computed radiography (CR) cassette.

The electronic cassette 13 is positioned in a posture in which the X-ray incident surface 13A that is an upper surface of the casing 22 faces the X-ray source 11, and the X-ray incident surface 13A is irradiated with X-rays. Although not shown, the casing 22 is also provided with a switch for switching between turning-on and turning-off of a main power source, and an indicator for reporting an operation state of the electronic cassette 13 such as a remaining battery usage time or an imaging ready state.

The sensor panel 20 is configured with a scintillator 20A and a light detection substrate 20B. The scintillator 20A and the light detection substrate 20B are laminated in the order of the scintillator 20A and the light detection substrate 20B when viewed from the X-ray incident surface 13A side. The scintillator 20A has phosphors such as CsI:Tl (thallium-activated cesium iodide) or GOS ($Gd_2O_2S$:Tb, terbium-activated gadolinium oxysulfide), and converts X-rays incident via the X-ray incident surface 13A into visible light and emits the visible light. A sensor panel in which the light detection substrate 20B and the scintillator 20A are laminated in this order when viewed from the X-ray incident surface 13A side may be used. A direct conversion type sensor panel that directly converts X-rays into signal charge with a photoconductor such as amorphous selenium may be used.

The light detection substrate 20B detects the visible light emitted from the scintillator 20A and converts the visible light into electric charge. The circuit unit 21 controls the drive of the light detection substrate 20B and generates the X-ray image XP on the basis of the electric charge output from the light detection substrate 20B.

A plurality of pixels are arranged in a two-dimensional matrix on the light detection substrate 20B. Each pixel photoelectrically converts the visible light emitted by the scintillator 20A to generate and store electric charge. The X-ray image XP is generated by converting the electric charge stored in each pixel into a digital signal in the circuit unit 21.

The electronic cassette 13 has a function of detecting, for example, the start of X-ray irradiation. This irradiation start detection function is realized by, for example, an irradiation start detection sensor provided on the light detection substrate 20B. The irradiation start detection sensor is configured with, for example, some of a plurality of pixels disposed in a two-dimensional matrix. In a case where a dose signal periodically output from the irradiation start detection sensor exceeds a threshold value, it is determined that the X-ray irradiation has started.

The electronic cassette 13 has a timer that starts clocking when the start of X-ray irradiation is detected, in the same manner as the radiation source control device 12. The electronic cassette 13 determines that the X-ray irradiation is finished when the time measured by the timer reaches the irradiation time included in the irradiation conditions set for the console 14. Consequently, the electronic cassette 13 can detect the X-ray image XP based on the applied X-ray by performing the X-ray detection operation only for a period corresponding to the irradiation time included in the irradiation conditions.

The electronic cassette 13 has an image memory and a wireless communication circuit. The electronic cassette 13 stores the X-ray image XP generated by the circuit unit 21 in the image memory, and transmits the X-ray image XP stored in the image memory to the console 14 with the wireless communication circuit.

Figure 3:
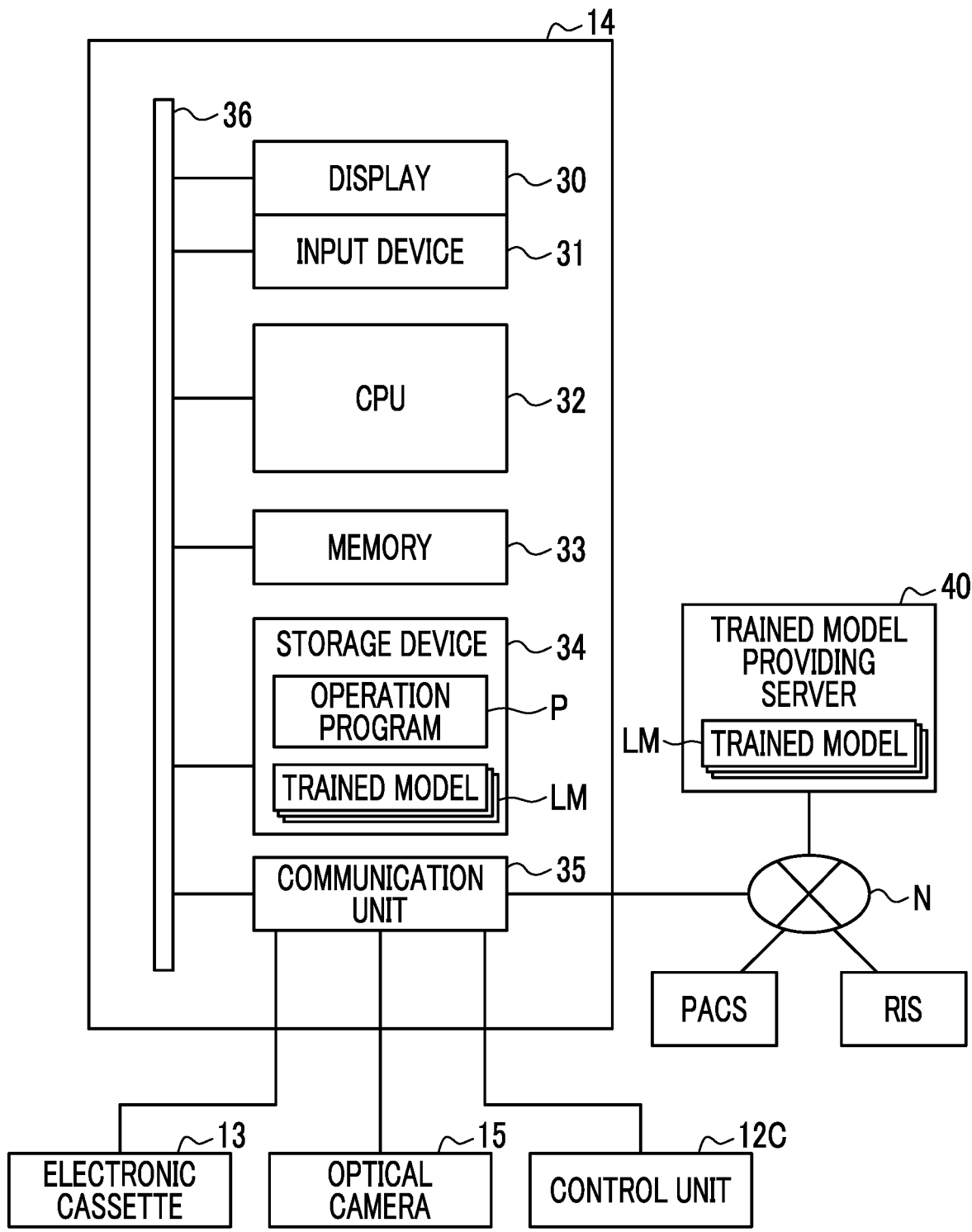
FIG. 3 is a block diagram showing a configuration of a console.

In FIG. 3, the console 14 includes a display 30, an input device 31, a central processing unit (CPU) 32, a storage device 34, a memory 33, and a communication unit 35. These constituents are connected to each other via a data bus 36.

The display 30 is a display that displays various operation screens provided with operation functions by a graphical user interface (GUI), the X-ray image XP, and the optical images (the still image SP and the motion picture MP). The input device 31 is an input operation unit including a touch panel, a keyboard, and the like.

The storage device 34 is, for example, a hard disk drive (HDD) array, which is built in the console 14 or externally connected to the console 14. External connection is made via a cables or a network. The storage device 34 stores control programs such as an operating system, various application programs, and various types of data associated with these programs.

The storage device 34 stores an operation program P for operating the console 14 and the optical camera 15 as an imaging support device, and a plurality of trained models LM provided by the trained model providing server 40. The storage device 34 stores a condition table 38 that will be described later and an image file 39 (refer to FIG. 6) including the X-ray image XP and the still image SP received from the electronic cassette 13.

The memory 33 is a work memory for the CPU 32 to execute a process. The CPU 32 collectively controls each unit of the console 14 by loading the program stored in the storage device 34 to the memory 33 and executing processes according to the program. The communication unit 35 transmits and receives various types of data such as the X-ray image XP and the optical images (the still image SP and the motion picture MP) to and from the electronic cassette 13 and the optical camera 15. The communication unit 35 communicates with the control unit 12C of the radiation source control device 12. The communication unit 35 communicates with the RIS, the PACS, and the trained model providing server 40 via the network N.

Figure 4:
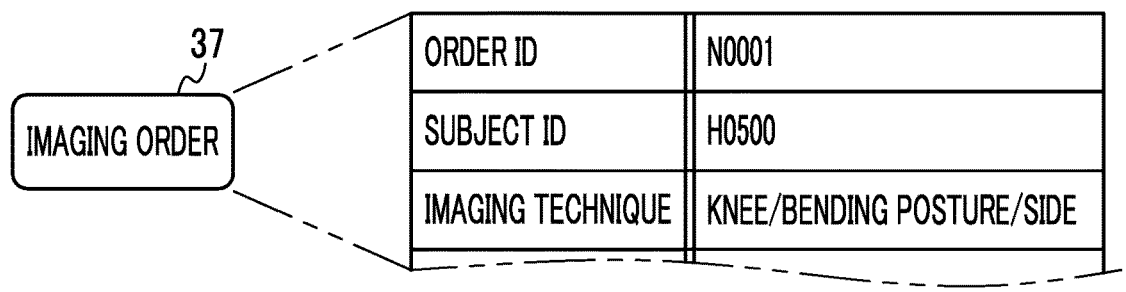
FIG. 4 is a diagram exemplifying an imaging order.

The console 14 receives input of an imaging order 37 shown in FIG. 4. The imaging order 37 is information for instructing the technician RG to perform X-ray imaging, for example, from an imaging requester in a clinical department. The imaging order 37 is delivered from the RIS to the console 14, for example.

The imaging order 37 has items such as an order identification data (ID), a subject ID, and an imaging technique. The order ID is a symbol or number that identifies each imaging order 37, and is automatically assigned by the RIS. In the item of subject ID, a subject ID of the subject H who is an imaging target is written. The subject ID is a symbol or a number that identifies each subject H.

The imaging technique is information regarding an imaging site of the subject H and a posture and an orientation of the imaging site. In addition to the knees exemplified in FIG.

1, the imaging site includes the head, the cervical spine, the chest, the abdomen, hands, fingers, elbows, and the like. The posture is a posture of the subject H such as a standing posture, a lying posture, or a sitting posture. The orientation is an orientation of the subject H with respect to the X-ray source 11, such as the front, the side, or the back. In addition to these items, the imaging order 37 includes items of subject information (patient information) such as the name, gender, age, height, and weight of the subject H.

Figure 5:
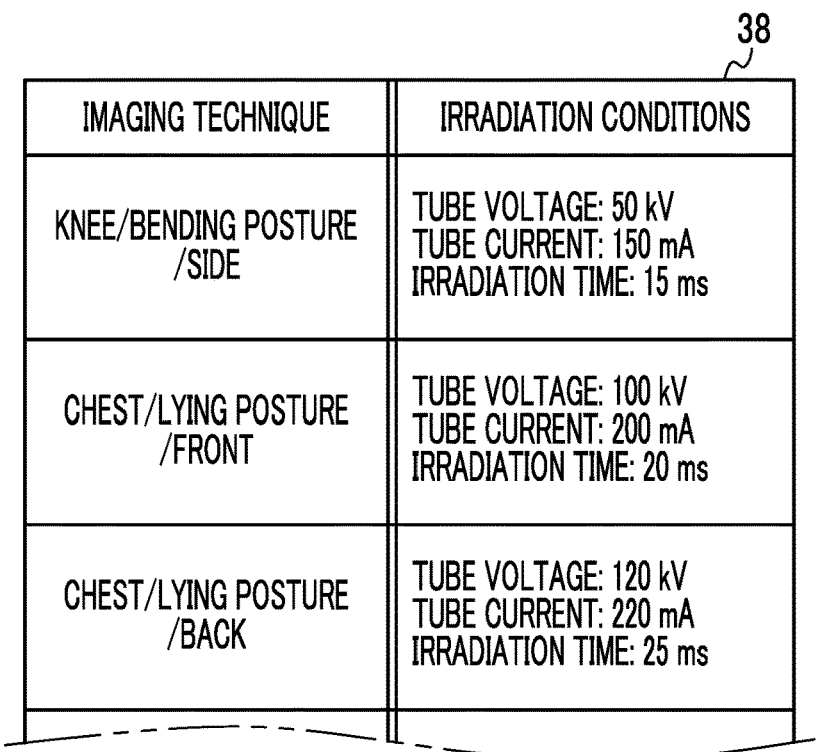
FIG. 5 is a diagram exemplifying a condition table.

The condition table 38 shown in FIG. 5 is stored in the storage device 34 of the console 14. Irradiation conditions corresponding to each imaging technique are associated and registered in the condition table 38.

The console 14 displays an imaging order list that lists the details of the imaging order 37 shown in FIG. 4 on the display 30 through an operation of the technician RG. The technician RG may view the imaging order list and check the details of the imaging order 37. The console 14 displays the details of the condition table 38 shown in FIG. 5 on the display 30. The technician RG may select and set irradiation conditions that match the imaging technique designated in the imaging order 37.

The console 14 wirelessly transmits condition setting signals including various types of information such as irradiation conditions set by the technician RG, an order ID, and a console ID as console identification information to the electronic cassette 13.

The console 14 stores the X-ray image XP received from the electronic cassette 13 in the storage device 34 that is a storage unit, for example, as an image file in a format conforming to the Digital Imaging and Communication in Medicine (DICOM) standard in association with the still image SP captured at the same as the X-ray image XP. The image file includes accessory information. The accessory information includes an order ID, a subject ID, an imaging technique, irradiation conditions, an imaging failure flag, a reason for imaging failure, and the like.

Figure 6:
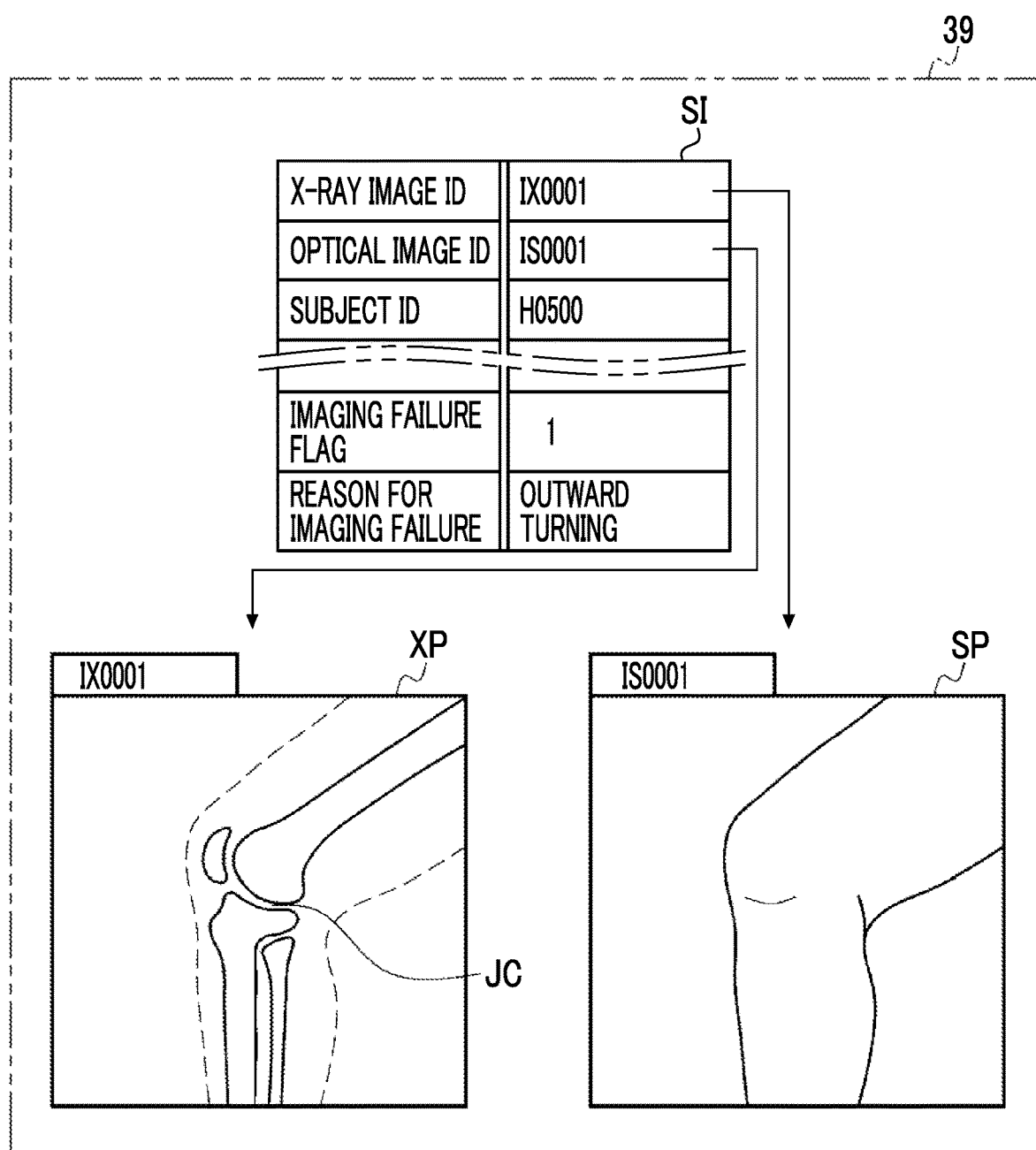
FIG. 6 is a diagram showing an example of an image file.

FIG. 6 shows an example of an image file stored in the storage device 34. As shown in FIG. 6, the image file 39 includes the X-ray image XP, the still image SP, and accessory information SI. The still image SP is assigned with an image ID (optical image ID) associated with an image ID (X-ray image ID) of the X-ray image XP captured at the same time. The X-ray image XP and the still image SP obtained when X-ray imaging is performed once are stored in one image file 39 in association with the X-ray image ID and the optical image ID.

The imaging failure flag included in the accessory information SI represents a determination result of whether or not the technician RG has determined that the imaging failure has occurred on the basis of the X-ray image XP displayed on the display 30. The technician RG may input the determination result by using the input device 31. For example, in a case where the imaging failure flag is "1", this means that the technician RG has determined that the X-ray image XP is an imaging failure image. On the other hand, in a case where the imaging failure flag is "0", this means that the technician RG has determined that the X-ray image XP is a normal image.

In a case where the imaging failure flag is "1", X-ray reimaging is performed, and in a case where the imaging failure flag is "0", X-ray reimaging is not performed. Thus, the imaging failure flag indicates whether or not an X-ray image has been captured again. The imaging failure flag is an example of result information according to the technique of the present disclosure.

The reason for imaging failure is a reason why the technician RG determines the occurrence of the imaging failure, and is input by the technician RG by using the input device 31.

In a case where the imaging technique is "knee/bending posture/side", a doctor makes a diagnosis of the joint cavity JC of the knee on the basis of the X-ray image XP. Thus, it is necessary that the joint cavity JC is clearly depicted in the X-ray image XP. For example, the technician RG determines whether or not the joint cavity JC is clearly depicted, and infers a reason why the imaging failure has occurred (reason for imaging failure).

Figure 7:
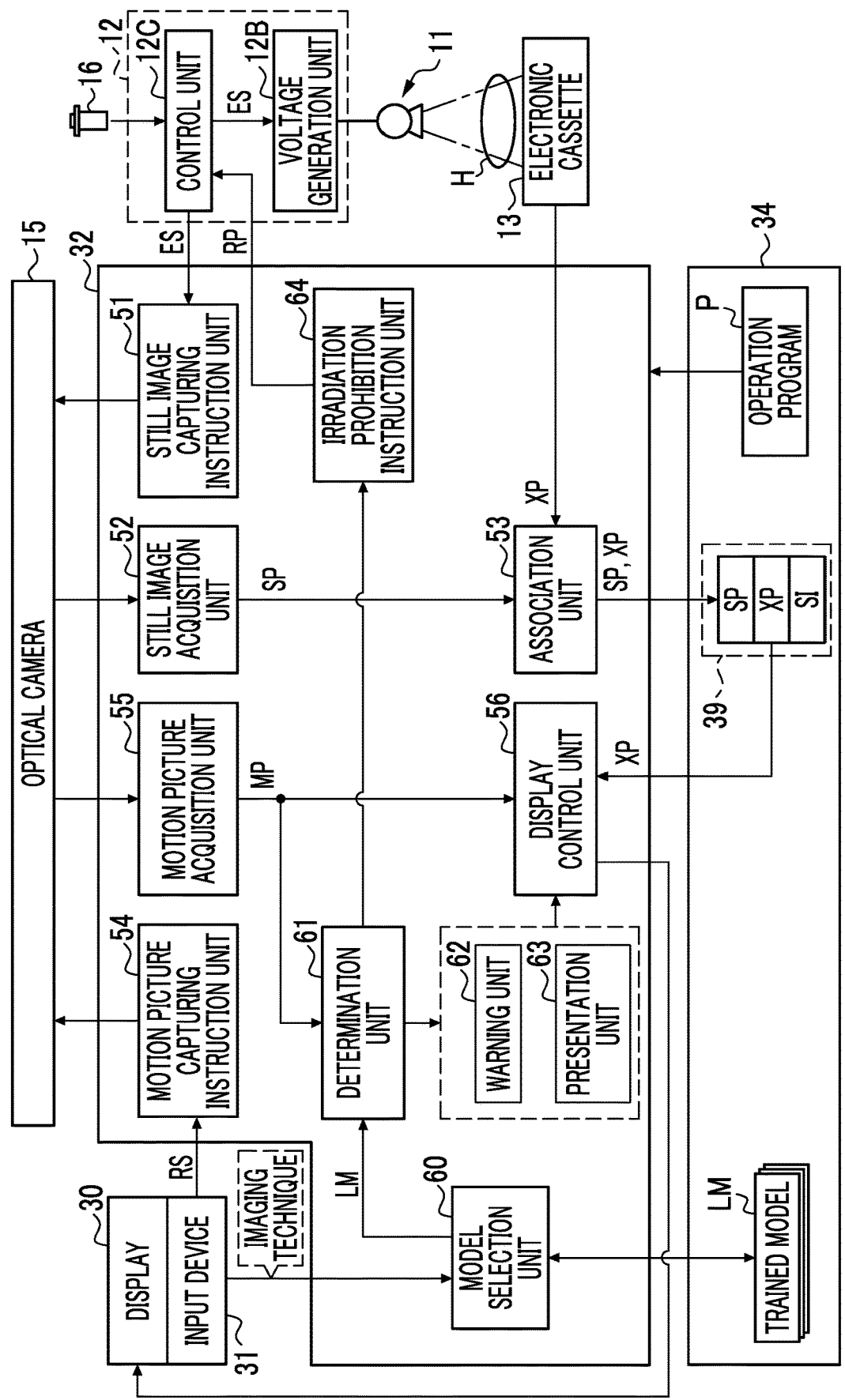
FIG. 7 is a block diagram showing each functional unit configured in a CPU.

FIG. 7 shows various functions configured in the CPU 32. The storage device 34 stores the operation program P. Although not shown, the condition table 38 shown in FIG. 5 is also stored in the storage device 34. A plurality of functional units are configured in the CPU 32 by executing the operation program P.

The operation program P causes the CPU 32 to function as a still image capturing instruction unit 51, a still image acquisition unit 52, an association unit 53, a motion picture capturing instruction unit 54, a motion picture acquisition unit 55, and a display control unit 56. The operation program P causes the CPU 32 to function as a model selection unit 60, a determination unit 61, a warning unit 62, a presentation unit 63, and an irradiation prohibition instruction unit 64.

The still image capturing instruction unit 51 receives an X-ray irradiation start signal ES generated by the control unit 12C of the radiation source control device 12 and supplied to the voltage generation unit 12B in response to the irradiation switch 16 being pressed. Upon receiving the X-ray irradiation start signal ES, the still image capturing instruction unit 51 instructs the optical camera 15 to execute still image capturing.

The still image acquisition unit 52 acquires the still image SP generated by the optical camera 15 capturing a still image. The still image SP acquired by the still image acquisition unit 52 is input to the association unit 53. The association unit 53 receives the X-ray image XP detected by the electronic cassette 13 on the basis of the X-rays emitted from the X-ray source 11 via the communication unit 35 (refer to FIG. 3) in response to the irradiation switch 16 being pressed.

The association unit 53 stores the image file 39 created by associating the still image SP input to the still image acquisition unit 52 with the X-ray image XP input from the electronic cassette 13 in the storage device 34. The image file 39 includes the above accessory information SI.

The motion picture capturing instruction unit 54 transmits a motion picture capturing start signal for instructing the optical camera 15 to start motion picture capturing in response to an imaging preparation start signal RS being input from the input device 31. The technician RG may cause the imaging support device to an X-ray imaging preparation mode by operating the input device 31 in a case of positioning the subject H as a preparatory step before performing X-ray imaging of the subject H.

The motion picture acquisition unit 55 acquires, in real time for each frame, the motion picture MP generated by the optical camera 15 capturing a motion picture. The motion picture acquisition unit 55 acquires an optical image for each frame and outputs the motion picture MP formed of a plurality of acquired frames. The motion picture MP output from the motion picture acquisition unit 55 is input to the display control unit 56 and the determination unit 61 for each frame.

The display control unit 56 displays the motion picture MP input from the motion picture acquisition unit 55 at the time of preparation for imaging on the display 30 for each frame (that is, real-time display). The display control unit 56 displays the X-ray image XP acquired through the X-ray imaging on the display 30.

The motion picture capturing of the optical camera 15 is finished in response to receiving an instruction for executing still image capturing from the still image capturing instruction unit 51 described above. The still image acquisition unit 52 may acquire one frame of the motion picture MP as the still image SP.

The technician RG may check the X-ray image XP displayed on the display 30, and in a case where it is determined that an imaging failure has occurred, operate the input device 31 to label the X-ray image XP as an imaging failure (that is, the imaging failure flag is set to "1").

The model selection unit 60 selects the trained model LM corresponding to the imaging technique included in the imaging order 37 selected by the technician RG by using the input device 31 from among the plurality of trained models LM stored in the storage device 34. The model selection unit 60 supplies the selected trained model LM to the determination unit 61.

The determination unit 61 uses the trained model LM supplied from the model selection unit 60 to perform a determination process on each frame of the motion picture MP input from the motion picture acquisition unit 55. The determination unit 61 determines whether or not there is a possibility that reimaging is necessary (that is, whether or not there is a possibility of reimaging) in a case where X-ray imaging is to be performed in a state of the subject H represented by each frame.

The trained model LM is configured by using a neural network. The trained model LM is configured by using, for example, a deep neural network (DNN), which is a multi-layer neural network that is a target of deep learning. As the DNN, for example, a convolutional neural network (CNN) for an image is used.

After performing the determination process, the determination unit 61 supplies the warning unit 62 with a "determination result" indicating whether or not there is a possibility that reimaging is necessary. In a case where it is determined that there is a possibility that reimaging is necessary, the determination unit 61 supplies a determination "reason" to the presentation unit 63. Hereinafter, the reason for determining that there is a possibility that reimaging is necessary will be referred to as a "reason for reimaging". As described above, in a case where the knee is used as an imaging site, "outward turning" or "inward turning" is the reason for reimaging. The determination unit 61 may generate a more detailed reason for reimaging.

On the basis of the determination result supplied from the determination unit 61, the warning unit 62 performs a warning notification process of supplying information indicating a warning to the display control unit 56 to be displayed on the display 30 in a case where there is a possibility that reimaging is necessary. That is, the warning unit 62 warns that in a case where X-ray imaging will be performed in the current positioning state of the subject H, there is a possibility that reimaging is necessary due to an imaging failure.

The warning unit 62 is not limited to displaying a warning on the display 30 of the console 14, and may display a warning on a device such as a mobile terminal connected to the X-ray imaging system 10. The warning unit 62 is not limited to the display on the display 30 or the like, and may provide a notification of a warning in sound or the like. A notification of a warning may be provided by using any method that stimulates the perception of the technician RG or the like.

The presentation unit 63 performs a presentation process of supplying information indicating the reason for reimaging supplied from the determination unit 61 to the display control unit 56 to be displayed on the display 30. The presentation unit 63 derives a corrective measure for correcting a position or an orientation of the subject H on the basis of the reason for reimaging, and supplies information indicating the derived corrective measure to the display control unit 56 to be displayed on the display 30. For example, in a case where the reason for reimaging is "inward turning", the presentation unit 63 derives a corrective measure that "it is better to turn outward", and conversely, in a case where the reason for reimaging is "outward turning", derives a corrective measure that "it is better to turn inward". The presentation unit 63 may derive a more detailed corrective measure.

The presentation unit 63 may display at least one of the corrective measure or the reason for reimaging on the display 30.

For example, the display control unit 56 superimposes and displays a message indicating the warning, the reason for reimaging, and the corrective measure on the motion picture MP displayed in real time on the display 30. The technician RG can prevent the occurrence of imaging failure by correcting the position or the orientation of the subject H on the basis of the message displayed on the display 30.

The determination unit 61 supplies the determination result to the irradiation prohibition instruction unit 64. The irradiation prohibition instruction unit 64 performs a prohibition process of supplying an irradiation prohibition signal RP to the control unit 12C of the radiation source control device 12 to prohibit irradiation with X-rays from the X-ray source 11 in a case where there is a possibility that reimaging is necessary on the basis of the determination result supplied from the determination unit 61. Consequently, in a case where there is a possibility that reimaging is necessary, interlock control in which the subject H is prohibited from being irradiated with X-rays is performed.

Figure 8:
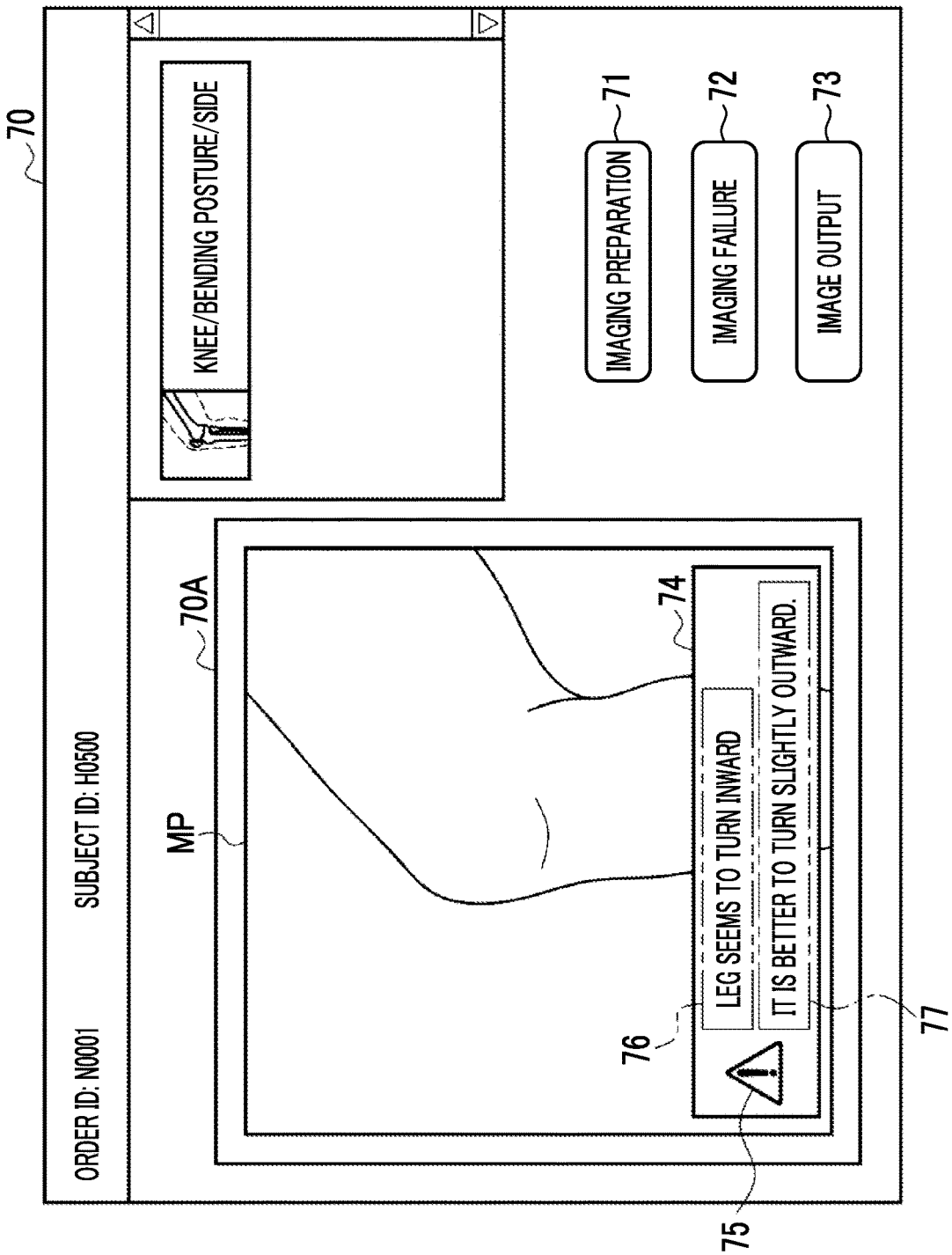
FIG. 8 is a diagram showing a display example of a console screen at the time of preparation for imaging.

FIG. 8 shows an example of a console screen displayed on the display 30 by the display control unit 56. As shown in FIG. 8, the console screen 70 is provided with an image display region 70A for displaying an image such as a motion picture MP or an X-ray image XP.

On the console screen 70, a first operation button 71 for starting imaging preparation, a second operation button 72 for labeling an imaging failure, and a third operation button 73 for outputting the image file 39 to the PACS are displayed. The first operation button 71, the second operation button 72, and the third operation button 73 are operated by a touch panel formed on the screen of the display 30.

FIG. 8 shows a display example of a console screen 70 at the time of preparation for imaging before X-ray imaging. The imaging preparation operation is started, for example, by the technician RG pressing the first operation button 71. In the example shown in FIG. 8, the motion picture MP obtained by the optical camera 15 is displayed in real time in an image display region 70A. In the image display region 70A, a message box 74 indicating a determination result or the like from the determination unit 61 is displayed.

In the example shown in FIG. 8, the message box 74 displays a warning mark 75 indicating that the determination result from the determination unit 61 is not good and there is a possibility that reimaging is necessary. The warning mark 75 is displayed on the basis of the warning information supplied from the warning unit 62 to the display control unit 56. In the message box 74, a reason for reimaging 76 and a corrective measure 77 supplied from the presentation unit 63 to the display control unit 56 are displayed.

The display content of the message box 74 is sequentially updated according to the determination result for each frame of the motion picture MP performed by the determination unit 61. The technician RG can correct the position or the orientation of the subject H on the basis of the display content of the message box 74. In a case where the determination result from the determination unit 61 is good because the subject H is properly positioned, for example, the message box 74 is not displayed.

Figure 9:
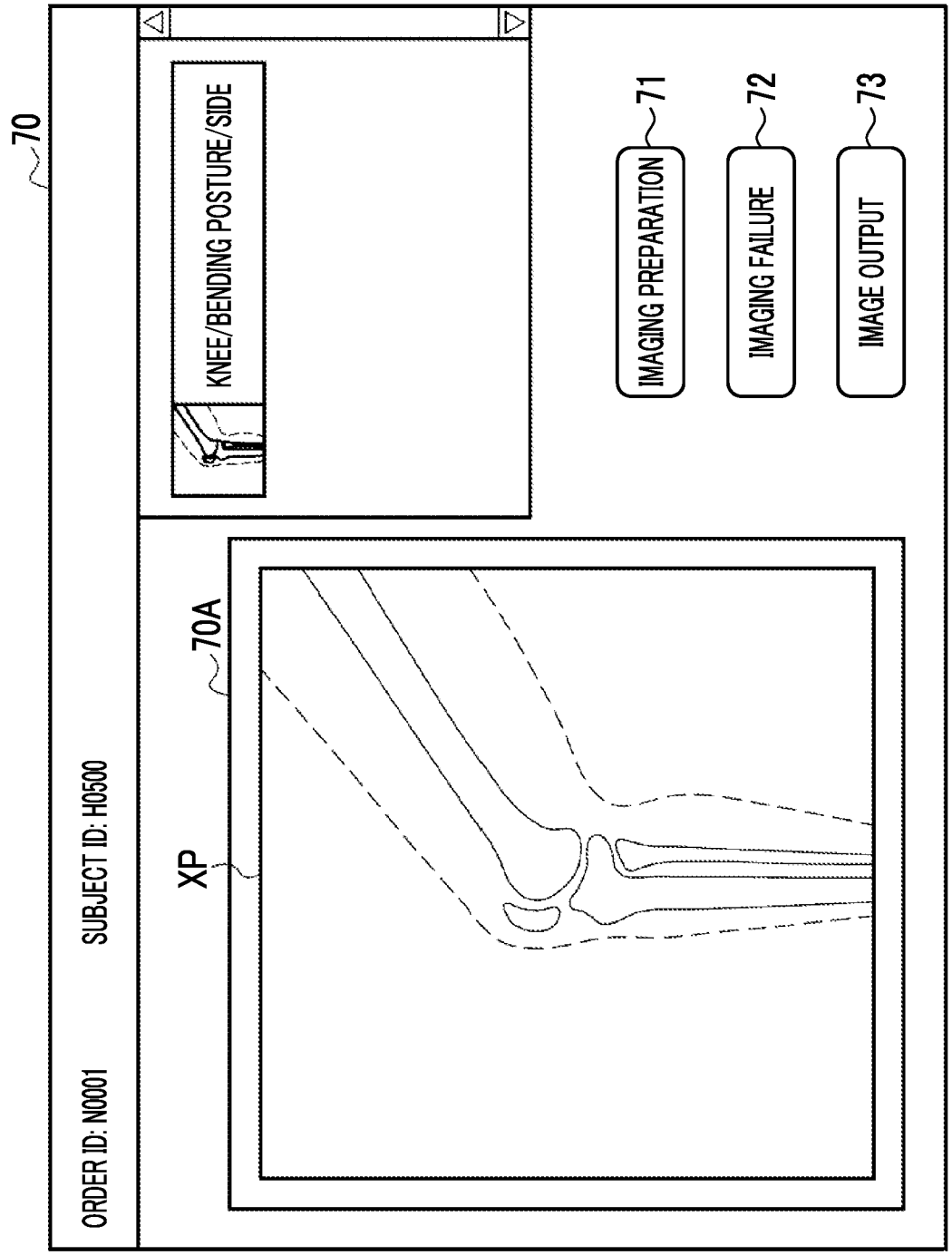
FIG. 9 is a diagram showing a display example of a console screen after X-ray imaging.

FIG. 9 shows a display example of the console screen 70 after X-ray imaging. In the example shown in FIG. 9, the X-ray image XP obtained through X-ray imaging is displayed in the image display region 70A. In a case where it is determined that the X-ray image XP is not an image suitable for diagnosis and reimaging is necessary (that is, imaging failure), the technician RG may press the second operation button 72 to label the X-ray image XP as an imaging failure image. Consequently, the imaging failure flag of the X-ray image XP included in the accessory information SI is set to "1". In this case, the technician RG may input the reason for the imaging failure by using a keyboard or the like (not shown).

In a case where the technician RG presses the third operation button 73, the above image file 39 including the X-ray image XP displayed in the image display region 70A is output to the PACS. The image file 39 including the X-ray image XP of which the imaging failure flag is set to "1" is output to the PACS or the imaging failure management system (not shown) via the network N.

Figure 10:
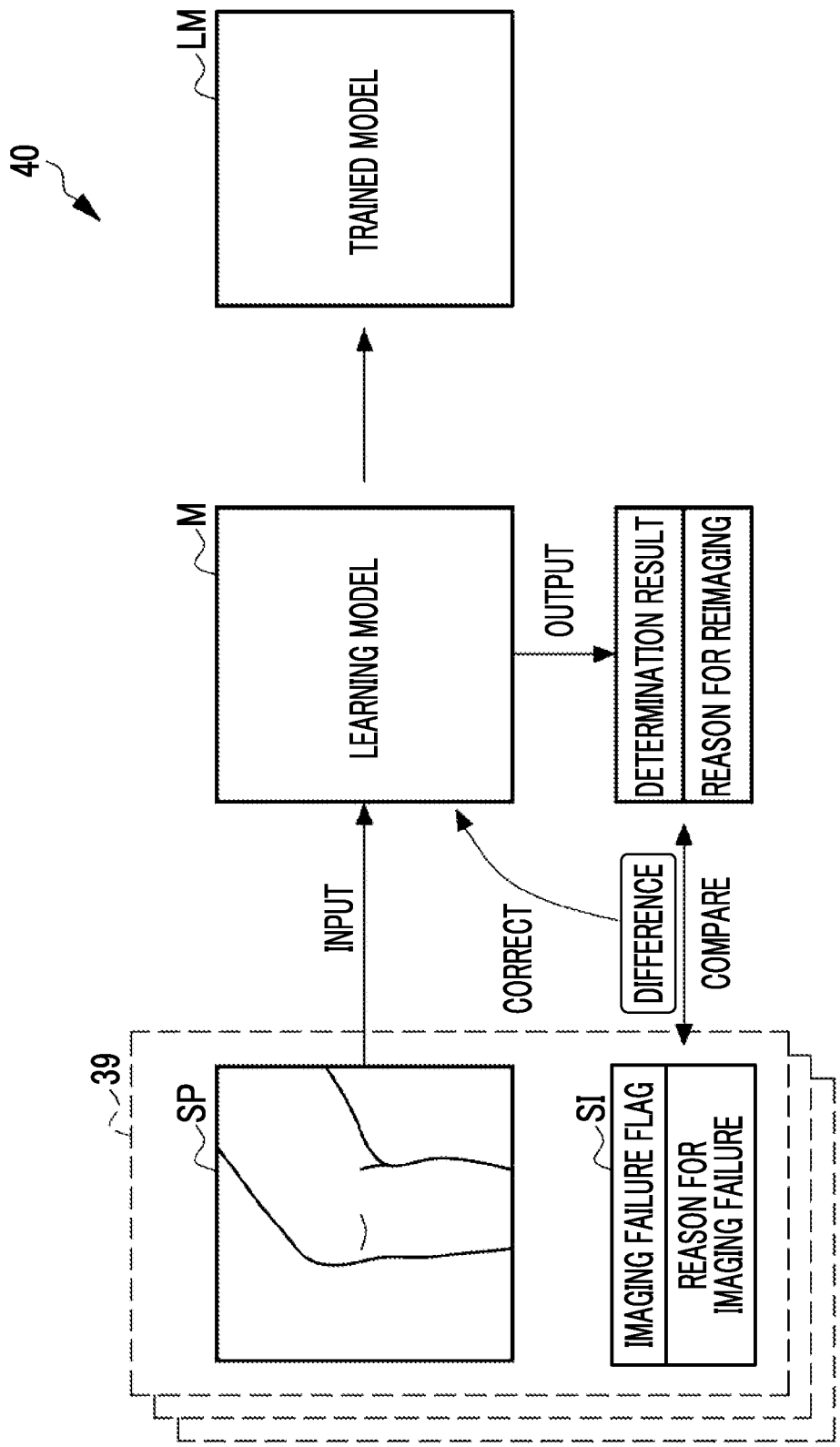
FIG. 10 is a diagram showing a process of generating a trained model.

FIG. 10 describes a process of generating the trained model LM. The generation of the trained model LM is executed by, for example, the trained model providing server 40. The trained model providing server 40 performs machine learning by using the image file 39 output to the PACS, the imaging failure management system, and the like.

As shown in FIG. 10, an untrained learning model M is stored in the trained model providing server 40. The still image SP included in the image file 39 is input to the learning model M. The learning model M outputs a determination result for the input still image SP and a reason for reimaging. The determination result and the reason for reimaging output from the learning model M are compared with the imaging failure flag and the reason for imaging failure as correct answer data included in the accessory information SI. Parameters of the learning model M are modified such that a difference between the two becomes small. By repeating the modification (that is, learning) of the parameters of the learning model M by using the plurality of image files 39, the trained model LM is obtained.

The trained model LM is generated for each imaging technique by using, for example, the image file 39 obtained according to the same imaging technique. The generation of the trained model LM is not limited to an external server such as the trained model providing server 40, and may be performed in the console 14. Each time the image file 39 is generated, the trained model LM may be updated by performing learning by using the generated image file 39. In order to reduce a load on the console 14, the trained model LM may be generated by a dedicated computer other than the console 14.

Figure 11:
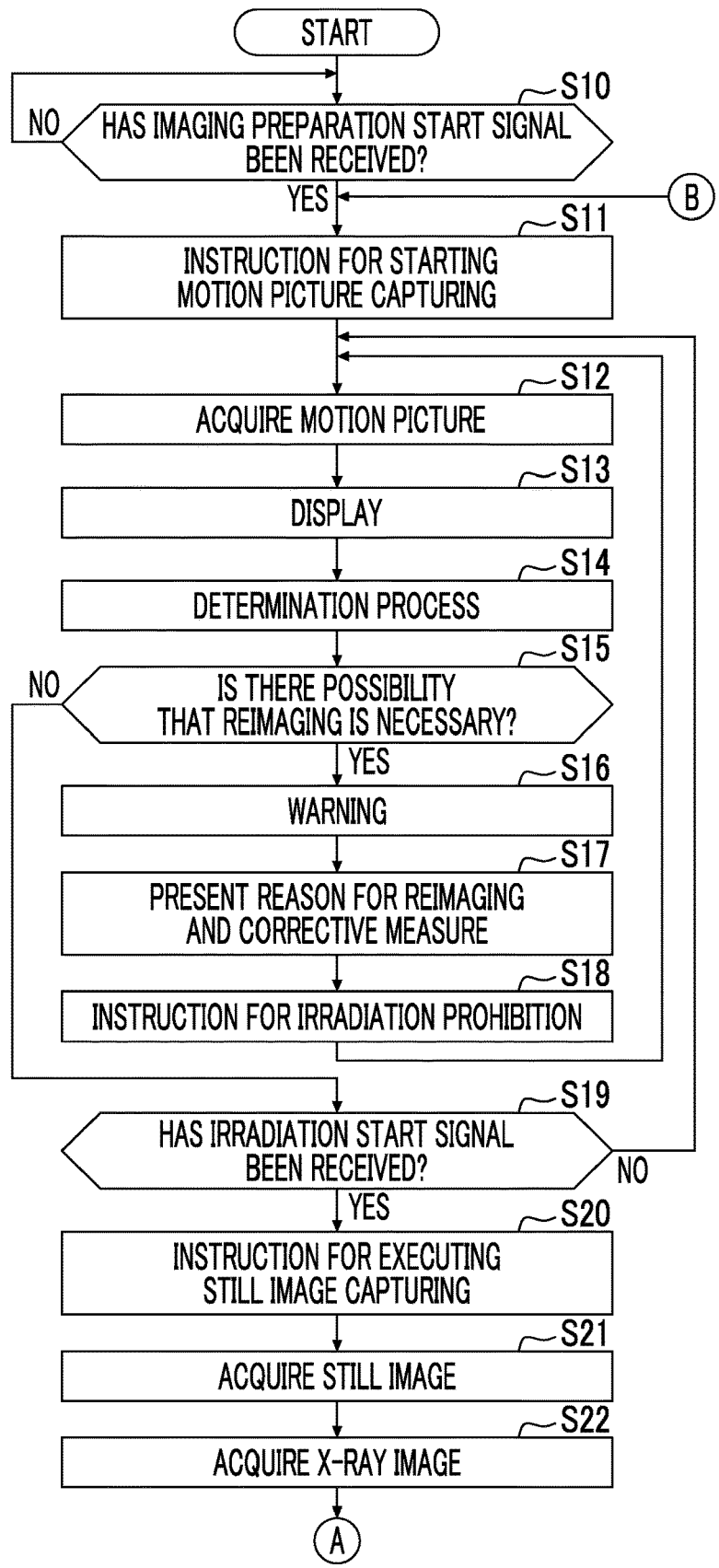
FIG. 11 is a flowchart for describing a first half part of a process procedure of the CPU.
Figure 12:
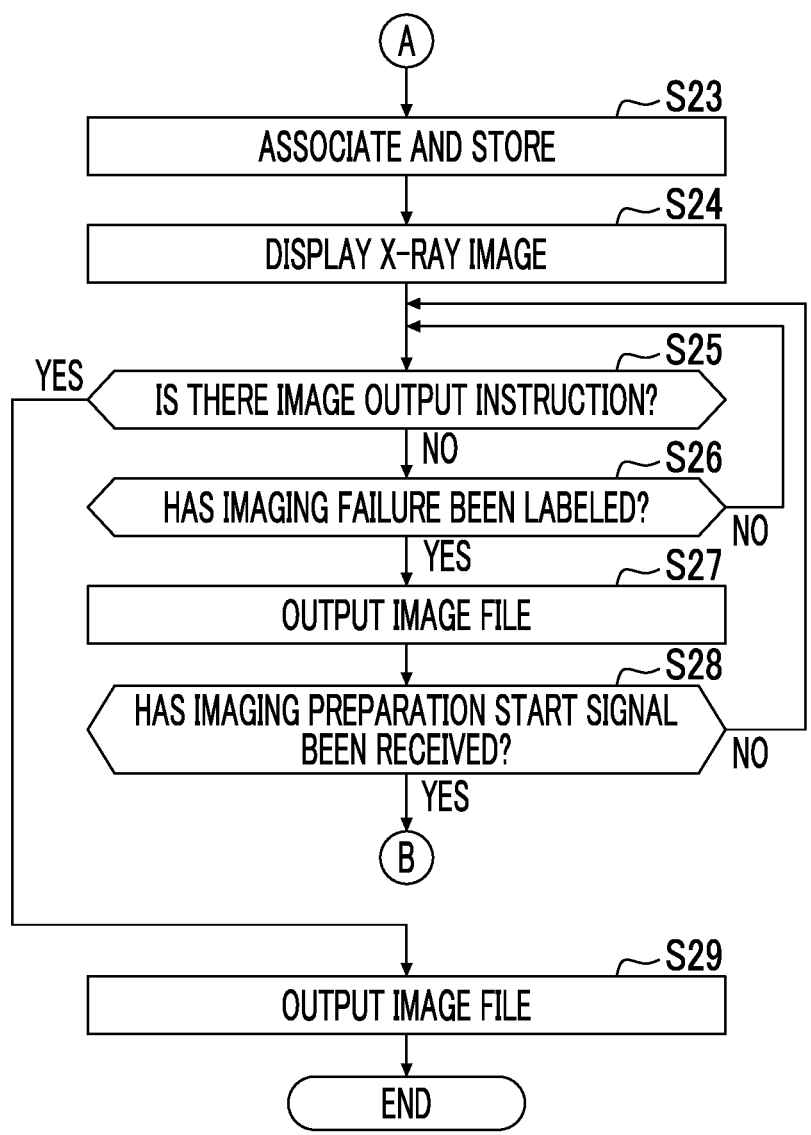
FIG. 12 is a flowchart for describing the second half part of the process procedure of the CPU.

Next, an operation of the imaging support device having the above configuration will be described with reference to flowcharts of FIGS. 11 and 12. First, prior to imaging, the technician RG checks details of the imaging order 37 on the display 30, and sets irradiation conditions by using the input device 31 and the touch panel 12A.

Next, the technician RG positions the X-ray source 11, the electronic cassette 13, and the subject H according to an imaging technique included in the imaging order 37. Here, the imaging technique is "knee/bending posture/side". The technician RG bends one leg of the subject H and positions the subject H such that the side of the knee faces the X-ray incident surface 13A of the electronic cassette 13 and the knee is located at the center of the irradiation field RF (refer to FIG. 1). The technician RG operates the imaging support device by pressing the first operation button 71 on the console screen 70 in a case of positioning the subject H. In a case where the first operation button 71 is pressed, the imaging preparation start signal RS is input from the input device 31 to the motion picture capturing instruction unit 54.

The motion picture capturing instruction unit 54 determines whether or not the imaging preparation start signal RS output from the input device 31 has been received by the technician RG pressing the first operation button 71 (step S10). In a case where it is determined that the imaging preparation start signal RS has been received (step S10: YES), the motion picture capturing instruction unit 54 transmits a motion picture capturing start signal to the optical camera 15 (step S11). The motion picture acquisition unit 55 acquires the motion picture MP generated by the optical camera 15 capturing a motion picture for each frame (step S12). The display control unit 56 displays the motion picture MP acquired by the motion picture acquisition unit 55 in the image display region 70A of the console screen 70 for each frame (step S13).

Each frame of the motion picture MP acquired by the motion picture acquisition unit 55 is supplied to the determination unit 61. The determination unit 61 performs a determination process on each frame of the motion picture MP by using the trained model LM selected by the model selection unit 60 (step S14). The model selection unit 60 selects the trained model LM corresponding to the imaging technique included in the imaging order 37.

The determination unit 61 determines whether or not there is a possibility that reimaging is necessary in a case where X-ray imaging is performed in a state of the subject H represented by each frame (step S15). In a case where the determination unit 61 determines that there is a possibility that reimaging is necessary (step S15: YES), the process proceeds to step S16.

In step S16, as shown in FIG. 8, the warning unit 62 warns that there is a possibility that reimaging is necessary by displaying the warning mark 75 in the image display region 70A. In the next step S17, the presentation unit 63 generates the reason for reimaging 76 and the corrective measure 77 on the basis of a determination result and a determination reason supplied from the determination unit 61 to be displayed in the image display region 70A. In the next step S18, the irradiation prohibition instruction unit 64 supplies the irradiation prohibition signal RP to the control unit 12C of the radiation source control device 12 to prohibit irradiation with X-rays from the X-ray source 11. After step S18 is finished, the process returns to step S12. The respective processes in steps S16 to S18 may be executed in parallel.

On the other hand, in a case where the determination unit 61 determines that there is no possibility that reimaging is necessary (step S15: NO), the process proceeds to step S19. That is, in a case where there is no possibility that reimaging is necessary, warning notification, presentation of the reason for reimaging and corrective measures, and prohibition of X-ray irradiation are not performed. In step S19, the still image capturing instruction unit 51 determines whether or not the X-ray irradiation start signal ES emitted from the control unit 12C has been received in response to the technician RG pressing the irradiation switch 16.

In a case where the still image capturing instruction unit 51 determines that the X-ray irradiation start signal ES has been received (step S19: YES), the process proceeds to step S20. On the other hand, in a case where the still image capturing instruction unit 51 determines that the X-ray irradiation start signal ES has not been received (step S19: NO), the process is returned to step S12.

In step S20, the still image capturing instruction unit 51 instructs the optical camera 15 to execute still image capturing. The still image acquisition unit 52 acquires the still image SP generated by the optical camera 15 capturing a still image (step S21). The console 14 acquires the X-ray image XP detected by the electronic cassette 13 (step S22).

Next, the association unit 53 stores the acquired X-ray image XP and still image SP in the storage device 34 in association with each other as the image file 39 along with the accessory information SI (step S23). The display control unit 56 displays the X-ray image XP in the image file 39 stored in the storage device 34 in the image display region 70A of the console screen 70 as shown in FIG. 9 (step S24).

Next, the CPU 32 determines whether or not an image output instruction has been given by the technician RG pressing the third operation button 73 (step S25). The technician RG checks the X-ray image XP displayed in the image display region 70A, and in a case where it is determined that reimaging is unnecessary, the technician RG gives an image output instruction by pressing the third operation button 73. In a case where it is determined that the third operation button 73 has been pressed (step S25: YES), the CPU 32 outputs the image file 39 stored in the storage device 34 to the PACS (step S29), and finishes the process.

On the other hand, in a case where it is determined that an image output instruction has not been given by the technician RG pressing the third operation button 73 (step S25: NO), the CPU 32 determines whether or not the X-ray image XP is labeled as an imaging failure by the technician RG pressing the second operation button 72 (step S26). This labeling includes input of a reason for imaging failure and the like.

In a case where it is determined that the X-ray image XP is labeled as an imaging failure (step S26: YES), the CPU 32 outputs the image file 39 including the X-ray image XP labeled as an imaging failure to the PACS or the imaging failure management system (step S27). On the other hand, in a case where the CPU 32 determines that the X-ray image XP is not labeled as an imaging failure (step S26: NO), the process returns to step S25.

In step S28, in the same manner as in step S10, the motion picture capturing instruction unit 54 determines whether or not the imaging preparation start signal RS output from the input device 31 has been received by the technician RG pressing the first operation button 71. In a case where the motion picture capturing instruction unit 54 determines that the imaging preparation start signal RS has been received (step S28: YES), the process proceeds to step S11. On the other hand, in a case where the motion picture capturing instruction unit 54 determines that the imaging preparation start signal RS has not been received (step S28: NO), the process returns to step S25. Thereafter, in a case where the CPU 32 determines that the third operation button 73 has been pressed (step S25: YES), the image file 39 is output to the PACS (step S29), and the process is finished.

As described above, in the imaging support device having the above configuration, a possibility of reimaging is determined by using the trained model at the time of preparation for imaging before X-ray imaging. Thus, according to the imaging support device having the above configuration, it is not necessary to register various positioning index images in advance and to select a positioning index image suitable for a subject unlike in the related art, and a technician or the like can easily ascertain a possibility of reimaging.

The determination unit 61 determines the motion picture MP input from the motion picture acquisition unit 55 for each frame, but may perform determination in units of a plurality of frames in order to reduce the processing load.

Each of the above embodiments has been described by exemplifying the X-ray imaging system provided in the imaging room, but the X-ray imaging system may be one using a so-called mobile visiting car.

The technique of the present disclosure can be applied not only to X-rays but also to a system for imaging a subject by using other radiation such as γ-rays.

In each of the above embodiments, hardware structures of processing units executing various processes, such as the still image capturing instruction unit 51, the still image acquisition unit 52, the association unit 53, the motion picture capturing instruction unit 54, the motion picture acquisition unit 55, the display control unit 56, the model selection unit 60, the determination unit 61, the warning unit 62, the presentation unit 63, and the irradiation prohibition instruction unit 64 are various processors as described below.

The various processors include a CPU, a programmable logic device (PLD), a dedicated electric circuit, and the like. As is well known, the CPU is a general-purpose processor that executes software (program) and functions as various processing units. The PLD is a processor such as a field programmable gate array (FPGA) of which a circuit configuration can be changed after manufacturing. The dedicated electric circuit is a processor having a circuit configuration specially designed for executing a specific process, such as an application specific integrated circuit (ASIC).

One processing unit may be configured with one of these various processors, or may be configured with a combination of two or more processors of the same type or different types (for example, a plurality of FPGAs or a combination of a CPU and an FPGA). A plurality of processing units may be configured by one processor. As an example of configuring a plurality of processing units with one processor, first, there is a form in which one processor is configured by a combination of one or more CPUs and software, as typified by a computer used for a client or a server, and this processor functions as a plurality of processing units. Second, as typified by system on chip (SoC), there is a form in which a processor that realizes functions of the entire system including a plurality of processing units with one integrated circuit (IC) chip is used. As described above, the various processing units are configured by using one or more of the above various processors as a hardware structure.

The hardware structure of these various processors is, more specifically, an electric circuit (circuitry) in which circuit elements such as semiconductor elements are combined.

It goes without saying that the present invention is not limited to each of the above embodiments, and various configurations can be employed without departing from the concept of the present invention. The present invention is applied not only to a program but also to a storage medium storing the program in a non-transitory manner.

What is claimed is:

1. An imaging support device used in a radiography apparatus including a radiation source and a radiation image detector that detects a radiation image of a subject on the basis of radiation emitted from the radiation source and transmitted through the subject, the imaging support device comprising:

an optical camera that outputs an optical image by optically imaging a region including an irradiation field of the radiation applied to the subject from the radiation source; and at least one processor, wherein the processor executes a determination process of determining a possibility of reimaging in a case where radiography is performed on the basis of the optical image acquired by the optical camera before start of the radiography by using a trained model that has learned a relationship between the optical image captured during the radiography and a necessity of recapturing the radiation image captured during the radiography.

2. The imaging support device according to claim 1, wherein the processor executes a warning notification process of providing a notification of a warning in a case where it is determined in the determination process that there is a possibility of reimaging.

3. The imaging support device according to claim 1, wherein the processor executes a prohibition process of prohibiting irradiation from the radiation source in a case where it is determined in the determination process that there is a possibility of reimaging.

4. The imaging support device according to claim 1, wherein the processor executes a presentation process of presenting a corrective measure for correcting a position or an orientation of the subject.

5. The imaging support device according to claim 4, wherein in the presentation process, the processor presents a reason for determining that there is a possibility of reimaging in addition to the corrective measure.

6. The imaging support device according to claim 5, wherein in the presentation process, the processor displays at least one of the corrective measure or the reason on a display.

7. The imaging support device according to claim 1, wherein the processor executes an association process of associating the optical image captured during the radiography with result information indicating whether or not the radiation image captured during the radiography has been recaptured.

8. An operation method for an imaging support device used in a radiography apparatus including a radiation source and a radiation image detector that detects a radiation image of a subject on the basis of radiation emitted from the radiation source and transmitted through the subject, the imaging support device including an optical camera that outputs an optical image by optically imaging a region including an irradiation field of the radiation applied to the subject from the radiation source, the operation method comprising:

determining a possibility of reimaging in a case where radiography is performed on the basis of the optical image acquired by the optical camera before start of the radiography by using a trained model that has learned a relationship between the optical image captured during the radiography and a necessity of recapturing the radiation image captured during the radiography.

9. A non-transitory computer-readable storage medium storing an operation program for operating an imaging support device used in a radiography apparatus including a radiation source and a radiation image detector that detects a radiation image of a subject on the basis of radiation emitted from the radiation source and transmitted through the subject, the imaging support device including an optical camera that outputs an optical image by optically imaging a region including an irradiation field of the radiation applied to the subject from the radiation source and at least one processor, the operation program causing the processor to execute:

a determination process of determining a possibility of reimaging in a case where radiography is performed on the basis of the optical image acquired by the optical camera before start of the radiography by using a trained model that has learned a relationship between the optical image captured during the radiography and a necessity of recapturing the radiation image captured during the radiography.

* * * * *